(12) United States Patent
Takehisa et al.

(10) Patent No.: US 9,991,670 B2
(45) Date of Patent: Jun. 5, 2018

(54) LASER LIGHT SOURCE DEVICE AND INSPECTION DEVICE

(71) Applicant: Lasertec Corporation, Yokohama, Kanagawa (JP)

(72) Inventors: Kiwamu Takehisa, Kanagawa (JP); Jun Sakuma, Kanagawa (JP)

(73) Assignee: Lasertec Corporation, Yokohama (JP)

( * ) Notice: Subject to any disclaimer, the term of this patent is extended or adjusted under 35 U.S.C. 154(b) by 401 days.

(21) Appl. No.: 14/626,005

(22) Filed: Feb. 19, 2015

(65) Prior Publication Data

US 2015/0244142 A1  Aug. 27, 2015

(30) Foreign Application Priority Data

Feb. 24, 2014  (JP) ................. 2014-032676

(51) Int. Cl.
*H01S 3/00*  (2006.01)
*H01S 5/00*  (2006.01)
(Continued)

(52) U.S. Cl.
CPC ....... *H01S 5/0092* (2013.01); *G01N 21/8806* (2013.01); *G01N 21/956* (2013.01);
(Continued)

(58) Field of Classification Search
CPC .. G01N 21/8806; G01N 21/956; G02F 1/353; G02F 2001/354; G03F 1/84;
(Continued)

(56) References Cited

U.S. PATENT DOCUMENTS 5,943,351 A      8/1999  Zhou et al.
2005/0265419 A1* 12/2005 Fujii .............. H04N 9/3129
                                                  372/96
(Continued)

FOREIGN PATENT DOCUMENTS

JP       2001-525946 A      12/2001

OTHER PUBLICATIONS

Sakuma, Jun, "DUV Laser Sources for Semiconductor Inspection Tools," Laser Engineering, vol. 41, No. 9, pp. No. 9, pp. 697-702, 2013.
(Continued)

*Primary Examiner* — Mohammed Rahaman
(74) *Attorney, Agent, or Firm* — Snyder, Clark, Lesch & Chung, LLP

(57) ABSTRACT

A laser light source device having a simple configuration and an inspection device are provided. A laser light source device 200 according to an exemplary embodiment in accordance with the present invention has a repetition frequency of 1 MHz or higher, and includes fundamental wave generation means 201 for oscillating laser light including a fundamental wave with its center wavelength being included in one of first to fourth wavelength bands, and means 205 for generating a sixth harmonic of pulsed laser light extracted from the fundamental wave generation means 201. The first wavelength band is 1064.326 nm to 1064.511 nm. The second wavelength band is 1064.757 nm to 1064.852 nm. The third wavelength band is 1063.805 nm to 1063.878 nm. Further, the fourth wavelength band is 1063.962 nm to 1064.031 nm.

7 Claims, 7 Drawing Sheets

(51) Int. Cl.
  *G02F 1/35*   (2006.01)
  *G01N 21/88*  (2006.01)
  *G01N 21/956* (2006.01)
  *G03F 1/84*   (2012.01)
  *G03F 7/20*   (2006.01)
  *H01S 3/16*   (2006.01)

(52) U.S. Cl.
  CPC .............. *G02F 1/353* (2013.01); *G03F 1/84* (2013.01); *G03F 7/7065* (2013.01); *G02F 2001/354* (2013.01); *H01S 3/1611* (2013.01); *H01S 3/1618* (2013.01)

(58) Field of Classification Search
  CPC .... G03F 7/7065; H01S 3/1611; H01S 3/1618; H01S 5/0092
  See application file for complete search history.

(56) References Cited

U.S. PATENT DOCUMENTS

| | | | | |
|---|---|---|---|---|
| 2006/0222372 | A1* | 10/2006 | Spinelli | H01S 3/2383 398/183 |
| 2007/0125298 | A1* | 6/2007 | Kolis | C30B 7/10 117/8 |
| 2008/0144148 | A1* | 6/2008 | Kusunose | G02B 27/0933 359/197.1 |
| 2010/0142032 | A1* | 6/2010 | Chen | C30B 9/12 359/329 |
| 2011/0032601 | A1* | 2/2011 | Kondo | G02F 1/39 359/330 |
| 2013/0313440 | A1* | 11/2013 | Chuang | G01N 21/956 250/372 |
| 2014/0111799 | A1* | 4/2014 | Lei | G01N 21/9501 356/237.5 |

OTHER PUBLICATIONS

Broadbent, William, et al., "EUV Reticle Inspection with a 193nm Reticle Inspector," Proceedings of SPIE vol. 8701, p. 8701W, 2013.

McMillen, Colin, et al., "Hydrothermal Growth and Properties of KBe2BO3F2 (KBBF) and RbBe2BO3F2 (RBBF) Single Crystals," 2010 OSA Optics and Photonics Congress, NThC6, 2010.

Kilmer, J. et al., "Laser Sources for Raman Spectroscopy," Proceedings of SPIE vol. 8039, p. 803914, 2011.

"Characteristics and Use of FFT-CCD Area Image Sensor," technical material, Hamamatsu Photonics K.K.

Held, Andrew, et al., "Quasi-CW Solid-State Lasers: Expand Their Reach," Technical material of Spectra-Physics, Photonics Spectra, Dec. 2002.

Friedman, H., Physics of the Upper Atmosphere, John Ashworth Ratcliffe, Academic Press, 1960.

Royon, Romain, et al., "High power, continuous-wave ytterbium-doped fiber laser tunable from 976 to 1120 nm," Optical Society of America, Optics Express 13818, 2013.

Matsui, T. et al., "High resolution absorption cross-section measurements of the Schumann-Runge bands of 02 by VUV Fourier transform spectroscopy," Journal of Molelcular Spectroscopy, vol. 219, pp. 45-57, 2003.

Zhang, Xin, et al., "High-power sixth-harmonic generation of an Nd:YAG laser with KBe2BO3F2 prism-coupled devices," Optics Communications, vol. 285, Issues 21-22, Oct. 1, 2012, pp. 4519-4522.

Office Action dated Aug. 19, 2014, in corresponding JP Patent Application No. 2014-032676, 2 pages.

* cited by examiner

LASER LIGHT SOURCE DEVICE AND INSPECTION DEVICE

INCORPORATION BY REFERENCE

This application is based upon and claims the benefit of priority from Japanese patent application No. 2014-32676, filed on Feb. 24, 2014, the disclosure of which is incorporated herein in its entirety by reference.

BACKGROUND OF THE INVENTION

1. Field of the Invention

The present invention relates to a laser light source device and an inspection device.

2. Description of Related Art

Generally speaking, there are two widely known methods for inspecting masks for defects, i.e., a comparison inspection method in which a mask pattern is compared with design data (which is commonly called "Die-to-database comparison method") and a pattern comparison inspection method in which same parts of two chips are compared with each other (which is commonly called "Die-to-die comparison method"). In either case, a pattern that is detected (i.e., obtained) by magnifying and projecting a microscopic part in a mask pattern on an image sensor surface of a CCD camera, a TDI camera, or the like by using an objective lens and a projecting lens is compared with design data or another pattern. It should be noted that it is necessary to illuminate the observation area on the mask pattern surface, and various ultraviolet-range laser devices are used as the light source for the illumination (which are commonly called "mask inspection light sources"). An outline of this technical matter is explained in, for example, the below-shown Non-patent Literature 1.

In particular, as a high-sensitive mask inspection device using a short-wavelength laser, a pattern inspection device using an ultraviolet pulsed laser device having a wavelength of 193 nm as a mask inspection light source has been developed. This pattern inspection device is shown in, for example, the below-shown Non-patent Literature 2.

The resolution, which influences the repeatability of a mask pattern projected on the image sensor surface, is in proportion to the wavelength of the laser light for the illumination and in inverse proportion to the numerical aperture NA of the objective lens used in the projection optical system. Therefore, the resolution may be improved by using laser light having a shorter wavelength or an objective lens having a higher numerical aperture NA.

As a light source of light having a wavelength shorter than 193 nm, a fluorine molecule laser device, which performs a laser operation at a wavelength of about 157 nm, has been widely known. However, the repetition rate of the fluorine molecule laser device is low as described later. Therefore, it is conceivable to use the sixth harmonic of laser light that oscillates at a wavelength of 1064 nm, i.e., ultraviolet light having a wavelength of 177 nm.

In particular, it has been known that by using a nonlinear optical crystal such as a KBBF ($KBe_2BO_3F_2$) crystal or an RBBF ($RbBe_2BO_3F_2$) crystal, the sixth harmonic of a solid-state laser device having a wavelength of 1064 nm can be obtained (e.g., Non-patent Literature 10). Note that the KBBF crystal and the RBBF crystal are shown in the below-shown Non-patent Literature 3. Further, the below-shown Non-patent Literature 4 also mentions that laser light having a wavelength of 175 nm can be obtained by using the KBBF crystal or the RBBF crystal.

Meanwhile, for an inspection light source used in a pattern inspection device, a laser device capable of performing a continuous operation (called "CW operation", CW stands for Continuous Wave) or a laser device capable of performing a high repetitive operation equal to or higher than 1 MHz is often used in order to obtain a uniform projection image and to increase the inspection speed.

In particular, when a TDI (Time Delay Integration) camera is used, the mask is scanned while projecting an image on the image sensor surface of the TDI camera. Note that the TDI camera is an image pickup device in which CCD elements perform a TDI operation. For example, a TDI camera is explained in the below-shown Non-patent Literature 5.

In a TDI camera, signals are integrated in one direction in the image sensor, which usually has a rectangular shape, and the signals are thereby averaged. As a result, even when the energy of pulsed light generated by the mask inspection light source fluctuates to some extent, the influence of the fluctuations on the obtained pattern signals is reduced. Therefore, it is preferable to use a light source that emits pulsed light at a repetition rate much higher than 100 to 1,000 Hz, which are typical framerates in TDI cameras. In particular, a laser device capable of operating a pulse operation at a high repetition rate equal to or higher than 1 MHz is suitable as the mask inspection light source. It should be noted that a CW operation laser device may be used. However, there is no CW laser device that can output sufficient power to carry out a mask inspection in the order of several hundred mw or higher at a wavelength shorter than 193 nm.

The reason why a laser device having a high repetition rate of 1 MHz of higher is suitable as a mask inspection light source is explained hereinafter. Assume an example case where the number of pixels of an image sensor is 1,000 pixels in the vertical direction and 2,000 pixels in the horizontal direction, and the image sensor is operated at a framerate of 1,000 Hz. In the case where the scanning direction in the mask is in parallel with the vertical direction of the image sensor, by using a light source capable of operating at a rate of 1,000×1,000 pulses per second (i.e., 1 MHz), the obtained values are averaged over the number of pulses equivalent to the number of pixels in the longitudinal direction. That is, optical energy quantities corresponding to 1,000 pulses are integrated at the same point. Therefore, even if the pulse energy fluctuates to some extent, its influence is substantially negligible.

It has been widely known that excimer laser devices and fluorine molecule laser devices perform high power operations in ultraviolet ranges and are used as lithography light sources. However, the repetition rate of the excimer laser devices and fluorine molecule laser devices is around 6000 Hz at the highest. Therefore, their repetition rate is too low to be used as a light source of a pattern inspection device, thus making them unsuitable for the pattern inspection device.

Meanwhile, though depending on the application, a pulsed laser device capable of operating at a very high repetition rate of 1 MHz or higher can be used as if it is a laser device capable of performing a continuous oscillating operation (CW). Therefore, in the sense that such laser devices are Quasi-CW laser devices, they are often called "QCW (Quasi-CW) laser devices". Examples of the QCW laser devices include a solid-state laser device performing a mode-locked operation, and a laser device in which mode-locked operation solid-state laser light or laser light generated by a semiconductor laser device performing a pulse operation by performing a high-speed modulation is amplified by a fiber amplifier. For example, mode-locked laser devices of 76 to 100 MHz are commercially available from a number of laser device manufacturers. These QCW laser devices are suitable for inspection devices because they have a sufficiently high repetition frequency. A QCW laser device is shown in, for example, the below-shown Non-patent Literature 6.

Non-patent Literature 1: Sakuma Jun, DUV Laser Sources for Semiconductor Inspection Tools, Laser Engineering, Vol. 41, No. 9, pp. 697-707, 2013.

Non-patent Literature 2: Proceedings of SPIE Vol. 8701, p. 8701W, 2013.

Non-patent Literature 3: Colin McMillen, et al, "Hydrothermal Growth and Properties of $KBe_2BO_3F_2$ (KBBF) and $RbBe_2BO_3F_2$ (RBBF) Single Crystals, 2010 OSA Optics and Photonics Congress, NThC6, 2010

Non-patent Literature 4: J. Kilmer, et al., "Laser Sources for Raman Spectroscopy, "Proceedings of SPIE Vol. 8039, p. 803914, 2011

Non-patent Literature 5: Characteristics and Use of FFT-CCD Area Image Sensor, technical material, Hamamatsu Photonics K.K.

Non-patent Literature 6: technical material of Spectra-Physics, "Quasi-CW Solid-State Laser, "PHOTONICS SPECTRA, December 2002

Non-patent Literature 7: H. Friedman, Physics of the Upper Atmosphere, John Ashworth Ratcliffe, Academic Press, 1960

Non-patent Literature 8: Romain Royon, et al., "High power, continuous-wave ytterbium-doped fiber laser tunable from 976 to 1120 nm," OPTICS EXPRESS 13818, 2013

Non-patent Literature 9: T. Matsui, et al., High resolution absorption cross-section measurements of the Schumann-Runge bands of O2 by VUV Fourier transform spectroscopy, Journal of Molecular Spectroscopy, Vol. 219, pp. 45-58, 2003

Non-patent Literature 10: Xin Zhanga, Lirong Wanga, b, Xiaoyang Wanga, Guiling Wanga, Corresponding author contact information, E-mail the corresponding author, Yong Zhua, Chuangtian Chena, "High-power sixth-harmonic generation of an Nd:YAG laser with KBe2BO3F2 prism-coupled devices," Optics Communications, Volume 285, Issues 21-22, 1 Oct. 2012, Pages 4519-4522

However, the present inventors have found the following problem. When an ultraviolet light source having a wavelength of 177 nm is used as a mask inspection light source, the emitted ultraviolet light tends to be absorbed by oxygen contained in the air. Therefore, there is a concern that the laser light could be attenuated and thus necessary power could not be obtained. This is because, as shown in an absorption spectrum of oxygen shown in FIG. 8, the wavelength 177 nm is included in absorption bands called "Shumann-Runge Bands". Note that the absorption spectrum of oxygen shown in FIG. 8 is shown in Non-patent Literature 7.

One of the techniques for preventing the attenuation of laser light is to fill the area through which the laser light passes with nitrogen. However, to fill the area with nitrogen, it is necessary to construct the inspection device with an air-tight structure. Further, it is necessary to evacuate the device by using a vacuum pump and then to fill the device with nitrogen. That is, it is necessary to construct the inspection device having a structure strong enough to withstand the pressure difference of one atmosphere (hereinafter called a "vacuum-tight structure") so that the inspection device can be evacuated. This causes a problem that the device cost significantly increases.

Further, a large number of complicated optical components are used in the inspection device, and these optical components are fine-tuned by an engineer when the device is started up. For the fine-tuning, the engineer needs to open the cover of the device and look into the device. In this case, it is necessary to restore the pressure inside the vacuum chamber to the atmosphere for the fine-tuning, thus requiring a longer time for the fine-tuning.

The present invention has been made in view of these circumstances, and an object thereof is to provide a laser light source device capable of oscillating (i.e., generating) laser light that can efficiently propagate through the air, and an inspection device having a simple configuration.

SUMMARY OF THE INVENTION

A first exemplary aspect of an exemplary embodiment according to the present invention is a laser light source device including: a solid-state laser device that oscillates laser light including a fundamental wave with its center wavelength being included in one of first to fourth wavelength bands; and means for generating a sixth harmonic of pulsed laser light having a pulse width equal to or greater than 2 picoseconds extracted from the solid-state laser device, in which the first wavelength band is between $(1063.763+\Delta\lambda)$ nm and $(1063.921-\Delta\lambda)$ nm, the second wavelength band is between $(1063.921+\Delta\lambda)$ nm and $(1064.073-\Delta\lambda)$ nm, the third wavelength band is between $(1064.284+\Delta\lambda)$ nm and $(1064.553-\Delta\lambda)$ nm, the fourth wavelength band is between $(1064.715+\Delta\lambda)$ nm and $(1064.894-\Delta\lambda)$ nm, and $\Delta\lambda$ (nm) is a value calculated by $\Delta\lambda=1.66\times10^{-12}/\Delta T$ when the pulse width of the fundamental wave is represented by $\Delta T(s)$. As a result, it is possible to oscillate (i.e., generate) laser light that can efficiently propagate through the air.

Another exemplary aspect of an exemplary embodiment according to the present invention is a laser light source device including: a QCW (Quasi-CW) solid-state laser device that oscillates laser light including a fundamental wave with its center wavelength being included in a range between 1064.326 nm and 1064.511 nm, the QCW solid-state laser device having a repetition frequency of 1 MHz or higher; and means for generating a sixth harmonic of pulsed laser light extracted from the solid-state laser device.

Another exemplary aspect of an exemplary embodiment according to the present invention is a laser light source device including: a QCW (Quasi-CW) solid-state laser device that oscillates laser light including a fundamental wave with its center wavelength being included in a range between 1064.757 nm and 1064.852 nm, the QCW solid-state laser device having a repetition frequency of 1 MHz or higher; and means for generating a sixth harmonic of pulsed laser light extracted from the solid-state laser device.

Another exemplary aspect of an exemplary embodiment according to the present invention is a laser light source device including: a QCW (Quasi-CW) solid-state laser device that oscillates laser light including a fundamental wave with its center wavelength being included in a range between 1063.805 nm and 1063.878 nm, the QCW solid-state laser device having a repetition frequency of 1 MHz or higher; and means for generating a sixth harmonic of pulsed laser light extracted from the solid-state laser device.

Another exemplary aspect of an exemplary embodiment according to the present invention is a laser light source device including: a QCW (Quasi-CW) solid-state laser device that oscillates laser light including a fundamental wave with its center wavelength being included in a range between 1063.962 nm and 1064.031 nm, the QCW solid-state laser device having a repetition frequency of 1 MHz or higher; and means for generating a sixth harmonic of pulsed laser light extracted from the solid-state laser device.

In the above-described laser light source device, a laser device using a solid crystal or a fiber doped with Yb or Nd as a medium may be used as the solid-state laser device. They may perform a pulse operation by a current modulation of laser light, or a mode-locked operation using a semiconductor saturable mirror or the like. Further, an output may be amplified by providing an amplification stage. As a result, pulse oscillation laser light including a fundamental wave with its center wavelength being included in the first to fourth wavelength bands can be easily obtained.

Another exemplary aspect of an exemplary embodiment according to the present invention is an inspection device including the above-described laser light source device, and a photodetector that takes an image of a sample illuminated by the sixth harmonic generated by the laser light source device. This configuration does not require the vacuum-tight structure, thus enabling a simpler device configuration.

In the above-described inspection device, the photodetector may be a TDI camera. As a result, the fluctuations of the laser light can be reduced, thus enabling a more accurate inspection.

According to the present invention, it is possible to provide a laser light source device that can be used in the atmosphere, and an inspection device having a simple configuration.

The above and other objects, features and advantages of the present invention will become more fully understood from the detailed description given hereinbelow and the accompanying drawings which are given by way of illustration only, and thus are not to be considered as limiting the present invention.

DESCRIPTION OF THE EXEMPLARY EMBODIMENTS

Figure 1:
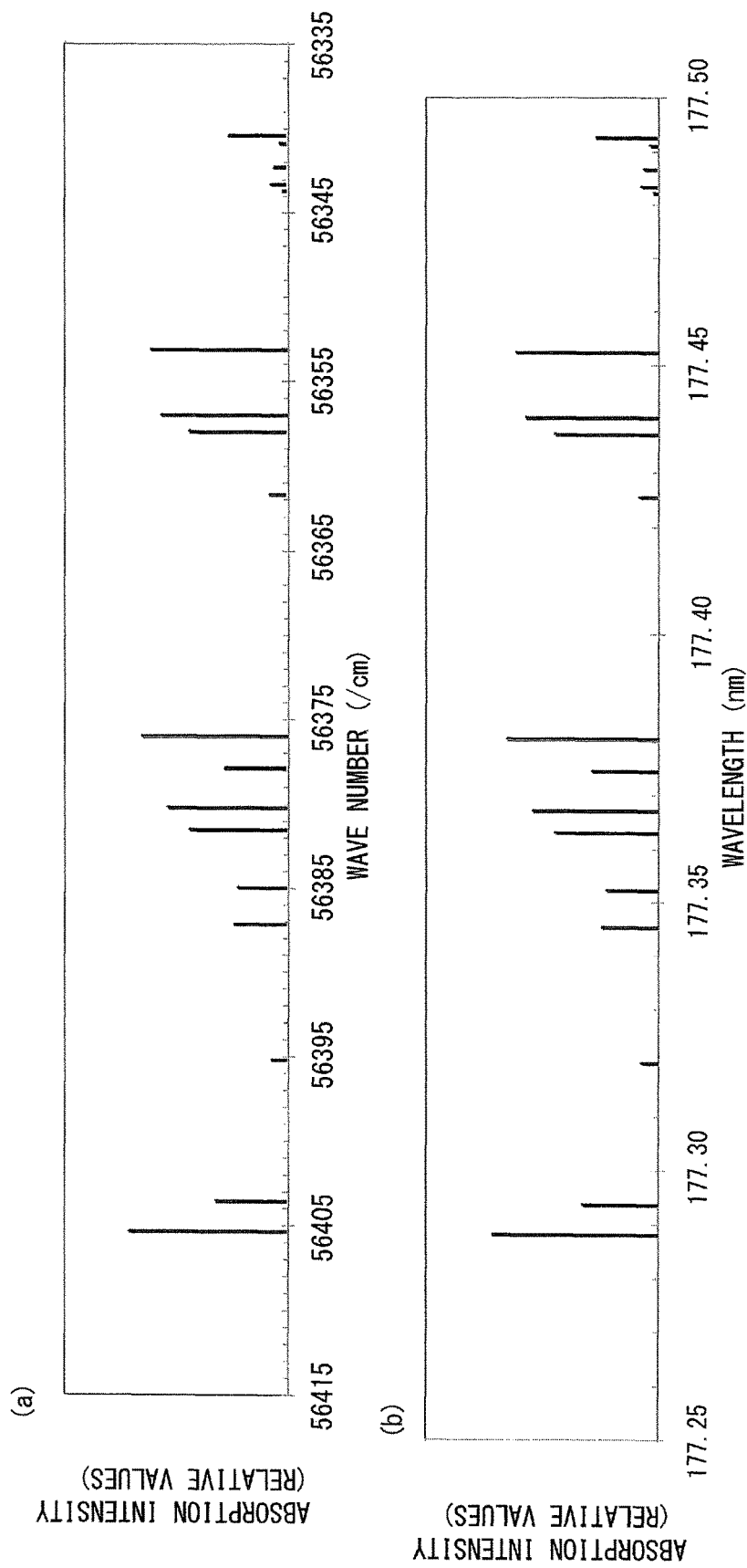
FIG. 1 shows spectra showing absorption lines of oxygen molecules.

To solve the above-described problem, a laser light source according to this exemplary embodiment includes a solid-state laser device that oscillates (i.e., generates) a fundamental wave at or near 1064 nm with its center wavelength being included in one of the below-shown four wavelength bands (hereinafter referred to as "bands [A] to [D]"), and sixth harmonic generation means for generating a sixth harmonic of the fundamental wave oscillated by the solid-state laser device. The band [A] is between $(1063.763+\Delta\lambda)$ nm and $(1063.921-\Delta\lambda)$ nm; the band [B] is between $(1063.921+\Delta\lambda)$ nm and $(1064.073-\Delta\lambda)$ nm; the band [C] is between $(1064.284+\Delta\lambda)$ nm and $(1064.553-\Delta\lambda)$ nm; and the band [D] is between $(1064.715+\Delta\lambda)$ nm and $(1064.894-\Delta\lambda)$ nm. The value $\Delta\lambda$ (nm) is a value calculated by $\Delta\lambda=1.66\times 10^{-12}/\Delta T$ when the pulse width is represented by $\Delta T(s)$.

The band [A] may be between 1063.805 nm and 1063.878 nm. The band [B] may be between 1063.962 nm and 1064.031 nm. The band [C] may be between 1064.326 nm and 1064.511 nm. The band [D] may be between 1064.757 nm and 1064.852 nm.

Examples of the solid-state laser device that oscillates at or near 1064 nm include a Yb-doped fiber laser device and an Nd-type solid-state laser device using an Nd:YVO4 crystal or an Nd:YAG crystal. Note that fiber laser devices are sometimes categorized separately from solid-state laser devices. However, in this specification of the present application, fiber laser devices are included in solid-state laser devices in the broad sense since their laser media are solid media.

It has been known that an Yb-doped fiber laser device can change its oscillation wavelength by several nm to several tens nm. Further, it has been known that in some cases, an Nd-type solid-state laser device can also change its oscillation wavelength by several nm. Therefore, it is possible to adjust the center wavelength so that it is included in one of the bands [A] to [D]. Note that the variable wavelength property of the Yb-doped fiber laser device is shown in Non-patent Literature 8.

When a pattern inspection device using a TDI camera is constructed, a QCW laser device capable of performing a high-speed operation of 1 MHz of higher is preferably used. In the case of a mode-locked laser device, the pulse width is included in a picosecond range or a femtosecond range. It has been known that the product of a pulse width $\Delta T$ and a spectrum width $\Delta v$ in the frequency domain is substantially determined based on the Fourier-limited pulse width as shown in the below-shown Expression (1).

$$\Delta\tau \times \Delta v \approx 0.441 \tag{1}$$

In Expression (1), the intensity distribution is assumed to be a Gauss distribution. In the expression, each of the pulse width $\Delta\tau$ and the spectrum width $\Delta v$ is a full width at half maximum (FWHM). Note that assuming that the wavelength is 1064 nm, when a spectrum width $\Delta\lambda$ (m) in the wavelength domain is used instead of the spectrum width $\Delta v$ in the frequency domain, a relation expressed by the below-shown Expression (2) is obtained.

$$\Delta\tau \times \Delta\lambda \approx 1.66 \times 10^{-21} \tag{2}$$

According to this relation, when the pulse width is 1 ps, the spectrum width $\Delta\lambda$ at the wavelength 1064 nm is $1.66 \times 10^{-9}$ m, i.e., 1.66 nm Since the frequency band of a wavelength 177 nm, which is a six-fold wave, is about $6^{0.5}$ (=2.45) times higher than the fundamental wave, this corresponds to 0.11 nm when converted into a wavelength.

Figure 2:
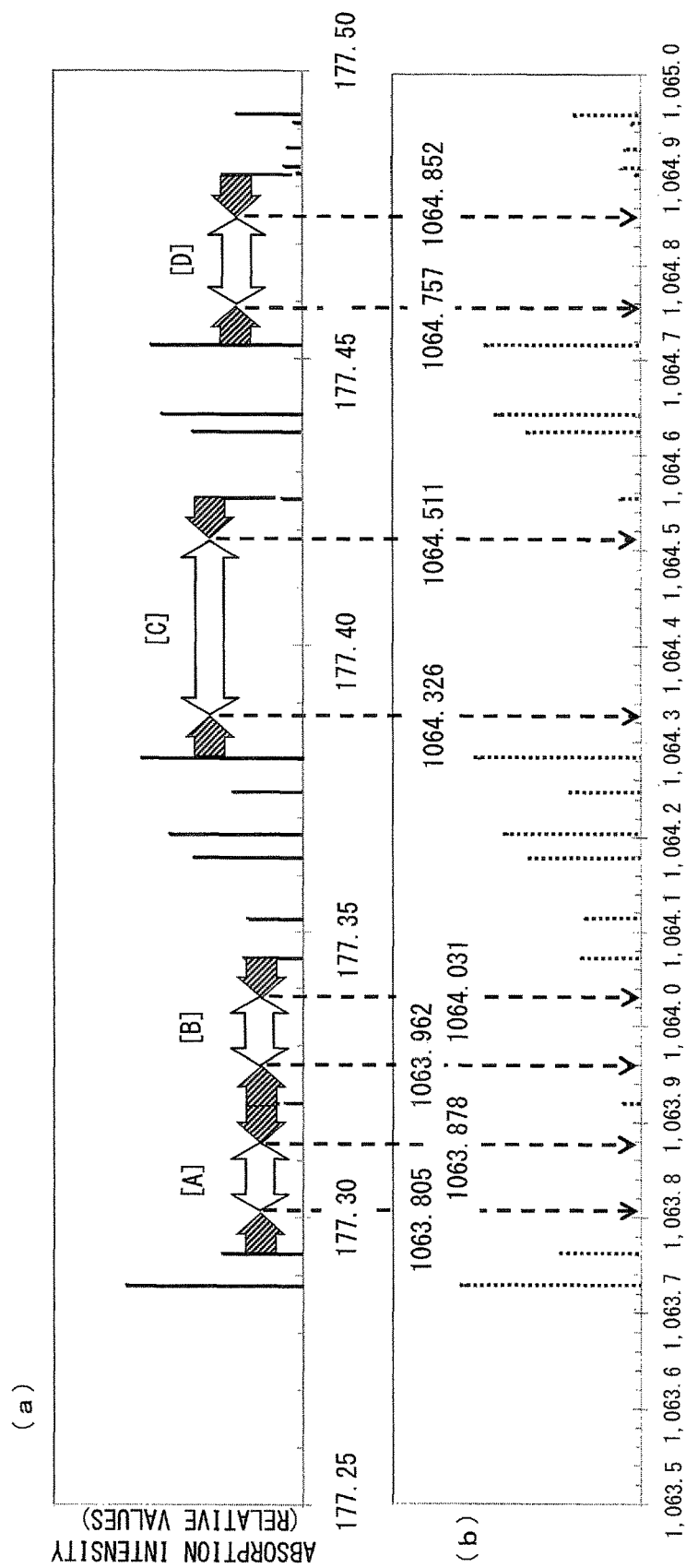
FIG. 2 shows spectra showing absorption lines of oxygen molecules and fundamental-wave-converted wavelengths.

Note that for the lower limit of the pulse width (i.e., the shortest pulse) of a solid-state laser device that can be used in the present invention, the only requirement is that the entire spectrum (two times the half-width) should be substantially contained in the widest interval [C] between two adjacent absorption lines (the interval is 44.9 pm) in the absorption spectrum of oxygen molecules shown in FIG. 2. In this case, the pulse full width at 177 nm is about 1.0 ps according to Expression (1). Therefore, with consideration given to the change of the pulse width due to the wavelength conversion ($6^{0.5}$ in the case of the six-fold wave), the pulse full width is about 2.5 ps for the fundamental wave. Accordingly, a solid-state laser device having a pulse width equal to or greater than 2.5 ps can be used. Note that when the pulse width decreases to about 2 ps, the spectrum width becomes wider. In some cases, there is a possibility that an absorption line could be included in the skirts (i.e., roughly horizontally extending parts) of the spectrum profile. However, since the power is low in the skirts pf the spectrum profile, the laser device can be used in the atmosphere without any problem, provided that the decreasing rate for the overall laser power is negligible. Therefore, a solid-state laser device having a short pulse width of about 2.0 ps can also be used.

FIG. 1 shows detailed structures of Shumann-Runge Bands in the absorption spectrum of oxygen molecules. (A) of FIG. 1 is a graph showing absorption intensities over wave numbers, and (b) of FIG. 1 shows a spectrum showing absorption intensities over wavelengths (nm) of a sixth harmonic. That is, (b) of FIG. 1 is obtained by associating the wave numbers ($cm^{-1}$) of the fundamental wave shown in (a) of FIG. 1 with the wavelengths (nm) of the sixth harmonic. Note that the absorption spectrum shown in FIG. 1 is shown in Non-patent Literature 9.

As can be seen from (b) of FIG. 1, there are a plurality of absorption lines between 177.25 nm and 177.50 nm Therefore, it can be understood that if the spectrum width (wavelength range) of the sixth harmonic laser light becomes 0.11 nm, it includes a number of absorption lines. To allow the sixth harmonic to propagate without loss, it is necessary to contain the spectrum width of the sixth harmonic within a range between two adjacent absorption lines. Therefore, it is necessary to narrow the spectrum width of the fundamental wave. In other words, based on Expression (2), it is necessary to increase the pulse width to a certain width or wider.

Meanwhile, it has been known that a picosecond laser device, which is included in commercially available QCW laser devices, oscillates (i.e., generates) laser light having a pulse width of about 5 to 20 ps. For example, when the spectrum width of laser light having a pulse width $\Delta\tau=8$ ps, as measured for the fundamental wave, is converted into a wavelength of 177 nm by using Expression (2), it becomes about 14 pm. As described above, by converting a fundamental wave having a pulse width of 8 ps in terms of its wavelength, a sixth harmonic having a spectrum width which spreads by ±7 pm from its center wavelength can be obtained. (A) of FIG. 2 shows an absorption spectrum of oxygen, and (b) of FIG. 2 shows a spectrum obtained by converting the absorption spectrum of oxygen in terms of the fundamental wave. In the absorption spectrum of oxygen shown in (a) of FIG. 2, the wavelengths of sixth harmonics corresponding to bands [A] to [D] are shown. That is, the ranges indicated by the outlined double-headed arrows correspond to the bands [A] to [D]. Further, the hatched arrows in the graph shown in (a) of FIG. 2 indicate that the bands are 7 pm away from the nearest absorption lines. By adjusting the center wavelength of the fundamental wave so as to be included in one of the bands [A] to [D], it is possible to make the sixth harmonic include no wavelength corresponding to absorption lines.

By including the center wavelength of the fundamental wave in one of the above-described bands [A] to [D] as described above, it is possible to make the sixth harmonic include no absorption line. That is, when each of the bands [A] to [D] is converted to the sixth harmonic on the condition that $\Delta T=8$ ps, the sixth harmonic includes no absorption lines in the range that is obtained by extending the lower end and the upper end of that band by an amount corresponding to a half of its spectrum width (7 pm) (i.e., the range between a wavelength 7 pm shorter than the lower end and a wavelength 7 pm longer than the upper end) as shown in (a) of FIG. 2. Therefore, no laser light is absorbed by oxygen molecules.

For example, in (a) of FIG. 2, no absorption line is included in a range between a wavelength 7 pm shorter than the lower end of the band [A] and a wavelength 7 pm longer than the upper end of thereof. Similarly, in (a) of FIG. 2, no absorption line is included in a range between a wavelength 7 pm shorter than the lower end of the band [B] and a wavelength 7 pm longer than the upper end thereof. In (a) of FIG. 2, no absorption line is included in a range between a wavelength 7 pm shorter than the lower end of the band [C] and a wavelength 7 pm longer than the upper end thereof. In (a) of FIG. 2, no absorption line is included in a range between a wavelength 7 pm shorter than the lower end of the band [D] and a wavelength 7 pm longer than the upper end thereof.

Therefore, by adjusting the center wavelength of the fundamental wave so that it is included in one of the bands [A] to [D], the wavelength-converted ultraviolet light is not absorbed by oxygen molecules. That is, a sixth harmonic having a spectrum width of ±7 pm from its center wavelength can propagate through the air without loss. This makes it possible to allow laser light to efficiently propagate even through the air. Therefore, there is no need to construct the inspection device with the vacuum-tight structure, thus enabling the use of a conventional inexpensive body.

A specific configuration of this exemplary embodiment is explained hereinafter with reference to the drawings. Preferable exemplary embodiments according to the present invention are explained in the following explanations. However, the scope of the present invention is not limited to the below-shown exemplary embodiments. In the following explanations, components/structures having the same symbols are components/structure substantially similar to each other.

Figure 3:
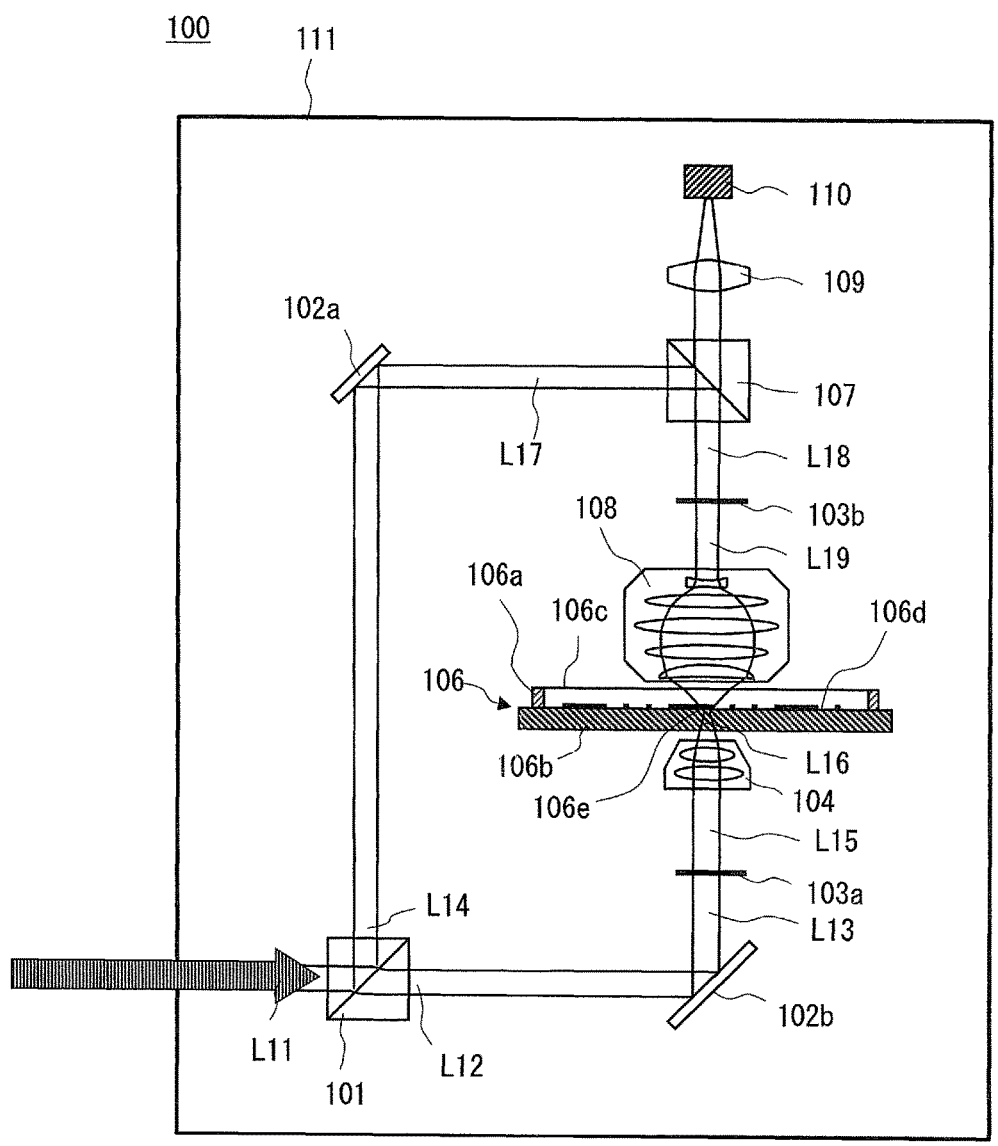
FIG. 3 is an overall configuration diagram of a mask inspection device according to an exemplary embodiment.

FIG. 3 is a configuration diagram showing a basic configuration of an inspection device 100. This exemplary embodiment is explained on the assumption that the inspection device 100 is a mask inspection device that inspects a mask 106.

The inspection device 100 includes a polarized light beam splitter 101, a mirror 102a, a mirror 102b, a λ/4-plate 103a, a λ/4-plate 103b, a condenser lens 104, a polarized light beam splitter 107, an objective lens 108, a projecting lens 109, and an optical detector 110. Further, the inspection device 100 includes a body cover 111 that contains the polarized light beam splitter 101, the mirror 102a, the mirror 102b, the λ/4-plate 103a, the λ/4-plate 103b, the condenser lens 104, the polarized light beam splitter 107, the objective lens 108, the projecting lens 109, and the optical detector 110.

An example of the mask 106, which is an object to be inspected, is a photomask used for a DUV (Deep UltraViolet) exposure. The mask 106 includes a mask substrate 106b, a pellicle frame 106a, a pellicle 106c, a pattern surface 106d, and a pattern 106e. A plurality of patterns 106e are arranged at regular intervals on the pattern surface 106d of the mask substrate 106b. Further, the pellicle frame 106a is disposed on the pattern surface 106d. The pellicle frame 106a is formed in the outer peripheral area of an exposure area where the patterns 106e are formed so that the pellicle frame 106a surrounds the exposure area. The pellicle 106c is tightly stretched over the surface of the pellicle frame 106a opposite to the pattern surface 106d. That is, the pellicle 106c is disposed in a position that is apart from the pattern surface 106d by a distance corresponding to the height of the pellicle frame 106a. The mask 106 is supported on a stage or the like (not shown).

The inspection device 100 uses laser light L11 having a wavelength 177 nm emitted from an inspection light source for the illumination. The configuration of a laser light source device, which serves as the inspection light source, is described later. The laser light L11, which is a linearly polarized light, is incident on the polarized light beam splitter 101 and is divided into two light beams traveling in different directions. One of the laser light beams divided by the polarized light beam splitter 101 serves as transmission illuminating light and the other serves as reflection illuminating light. That is, the inspection device 100 illuminates the mask, which is a sample, by the transmission lighting and the reflection lighting.

Firstly, the transmission lighting is explained. The laser light L12, which has passed through the polarized light beam splitter 101, is reflected on the mirror 102b and becomes laser light L13. The mirror 102b reflects the laser light L13 toward the mask 106. The laser light L13 passes through the λ/4-plate 103a and becomes laser light L15. The laser light L15, which has passed through the λ/4-plate 103a, is incident on the condenser lens 104 and becomes laser light L16. The condenser lens 104 concentrates the laser light L16 on the pattern surface 106d of the mask 106.

Specifically, after being refracted by the condenser lens 104, the laser light L16 travels while converging (i.e., becoming narrower) and then is incident on the mask 106. The laser light L16 passes through the mask substrate 106b and is incident on the pattern surface 106d. The laser light L16 illuminates an observation area on the pattern surface 106d of the mask 106. Note that each of the laser light L12 and L13 is a P-wave, and the laser light L13 is converted into counterclockwise circularly-polarized light, which is the laser light L15, by passing through the λ/4-plate 103a. Therefore, the laser light L16, which is also counterclockwise circularly-polarized light, illuminates the mask 106.

As the laser light L16 illuminates the observation area on the pattern surface 106d, diffracted light is generated according to the pattern 106e. Part of the diffracted light generated in the observation area travels toward the objective lens 108. After being refracted by the objective lens 108, the diffracted light is incident on the λ/4-plate 103b. Note that the diffracted light traveling toward the objective lens 108 is counterclockwise circularly-polarized light. Therefore, by passing through the λ/4-plate 103b, the diffracted light generated by the transmission lighting returns to the P-wave, which is the same as the original laser light L12. Since the diffracted light from the λ/4-plate 103b is the P-wave, it passes through the polarized light beam splitter 107.

The diffracted light, which has passed through the polarized light beam splitter 107, is incident on the projecting lens 109. The diffracted light is concentrated by the projecting lens 109 and reaches a sensor surface of the optical detector 110. That is, an image of the pattern 106e in the observation area of the pattern surface 106d is magnified and projected on the sensor surface of the optical detector 110. The optical detector 110 is a camera that takes an image of the observation area of the mask 106. The optical detector 110 is preferably a TDI camera.

Next, the reflection lighting is explained. The laser light L14, which has been reflected on the polarized light beam splitter 101 and is an S-wave, is reflected on the mirror 102a and becomes laser light L17. The laser light L17 is incident on the polarized light beam splitter 107. Note that since the laser light L17 is the S-wave, the laser light is reflected on the polarized light beam splitter 107 and becomes laser light L18. The laser light L18, which has been reflected on the polarized light beam splitter 107, travels downward and toward the mask 106. The laser light L18 passes through the λ/4-plate 103b and becomes laser light L19. By passing through the λ/4-plate 103b, the laser light L18 becomes clockwise circularly-polarized light, which is the laser light L19. The laser light L19 is incident on the objective lens 108 and illuminates the pattern surface 106d. The objective lens 108 concentrates the laser light L19 on the pattern surface 106d.

The observation area on the pattern surface 106d is illuminated by the above-described reflection lighting. The reflected light reflected on the observation area on the pattern surface 106d becomes counterclockwise circularly-polarized light. Then, the reflected light passes through the objective lens 108 and the λ/4-plate 103b. Since the reflected light passes through the λ/4-plate 103b again, it becomes a P-wave. Therefore, the reflected light, which has passed through the λ/4-plate 103b, passes through the polarized light beam splitter 107. The reflected light passes through the projecting lens 109 and is magnified and projected on the sensor surface of the optical detector 110. The optical detector 110 takes an image of the mask 106 illuminated by the reflection illuminating light.

Note that the reflection lighting and the transmission lighting may be simultaneously performed. Alternatively, the mask 106 may be illuminated by only one of them. A pattern inspection of the mask 106 is performed according to image results taken by the optical detector 110. Note that the Die-to-database comparison method or the Die-to-die comparison method, for example, may be used for the pattern inspection. Since these comparison methods are similar to those used in the related art, their explanations are omitted.

Figure 4:
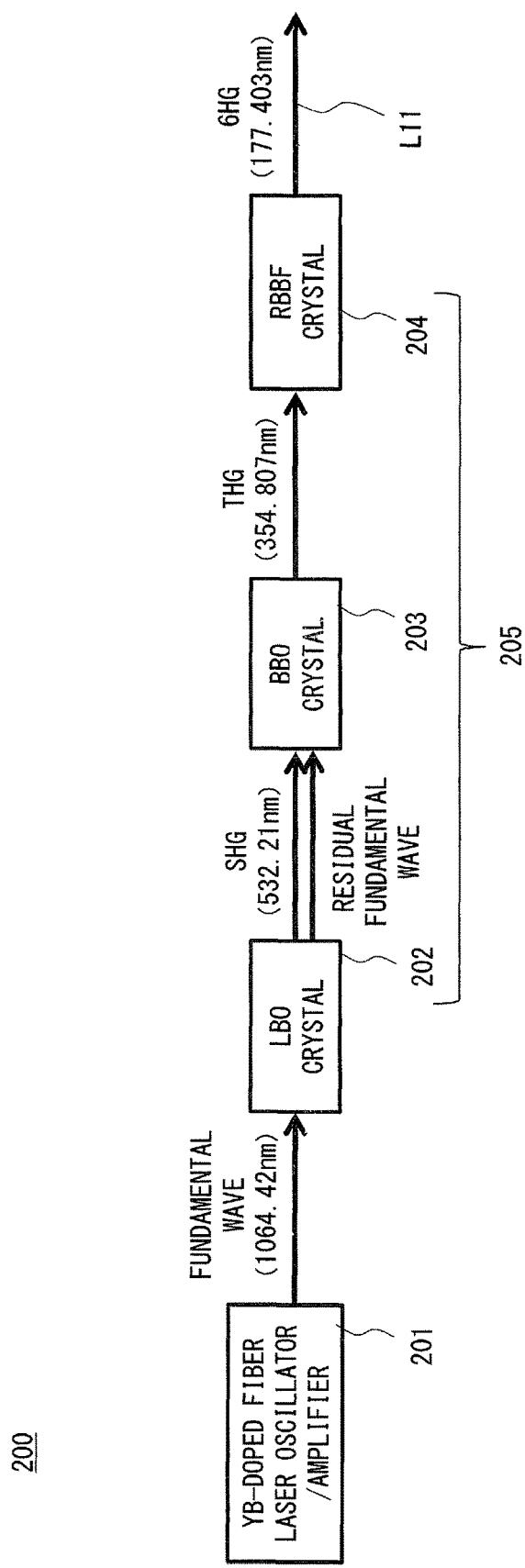
FIG. 4 is a configuration diagram of a light source used in a mask inspection device.

Next, a laser light source device that emits the laser light L11 having a wavelength 177 nm is explained with reference to FIG. 4. FIG. 4 is a configuration diagram of a laser light source device 200 according to the present invention. The laser light source device 200 includes fundamental wave generation means 201 and sixth harmonic generation means 205. The sixth harmonic generation means 205 includes an LBO (LiB$_3$O$_5$) crystal 202, a BBO (β-BaB$_2$O$_4$) crystal 203, and an RBBF crystal 204, and generates the sixth harmonic of the fundamental wave.

In the laser light source device 200, an Yb-doped fiber laser device is used for the fundamental wave. That is, an Yb-doped fiber laser oscillator/amplifier is used as the fundamental wave generation means 201. The center wavelength of an Yb-doped fiber laser device is fixed to 1064.42 nm. Further, the Yb-doped fiber laser device performs a QCW operation to oscillate (i.e., generate) laser light and its pulse width is about 8 ps. For example, the Yb-doped fiber laser device generates pulsed laser light at a repetition frequency of 1 MHZ or higher.

The fundamental wave (wavelength 1064.42 nm) is incident on the LBO crystal 202. The LBO crystal 202 serves as SHG (Second Harmonic Generation) means. That is, the LBO crystal 202 generates laser light having a wavelength 532.21 nm, which is the second harmonic of the fundamental wave. The second harmonic from the LBO crystal 202 and the unconverted fundamental wave (residual fundamental wave) are both incident on the BBO crystal 203. The BBO crystal 203 serves as SFG (Sum Frequency Generation) means and generates the third harmonic (wavelength 354.807 nm). That is, the BBO crystal 203 generates laser light of the third harmonic (wavelength 354.807 nm), which is the sum frequency of the residual fundamental wave (wavelength 1064.42 nm) and the second harmonic (wavelength 532.21 nm).

The third harmonic (wavelength 354.807 nm) is incident on the RBBF crystal 204. The RBBF crystal 204 serves as SHG (Second Harmonic Generation) means. Therefore, the RBBF crystal 204 generates the sixth harmonic (wavelength 177.403 nm) from the third harmonic (wavelength 354.807 nm).

The above-described fundamental wave wavelength (1064.42 nm), the second harmonic wavelength (532.21 nm), the third harmonic wavelength (354.807 nm), and the sixth harmonic wavelength (177.403 nm) are the center wavelengths of their respective laser light beams.

The spectrum width (full width at half maximum) of the laser light L11 having the center wavelength of 177.403 nm is about 14 pm. Further, when the skirts of its profile are included, the laser light L11 spreads over about 30 pm (see FIG. 5). The entire profile of the laser light L11 is away from any absorption lines of oxygen molecules shown in FIG. 5. Therefore, the laser light is not absorbed by oxygen molecules. Accordingly, the laser light L11 propagates even through the air without loss.

The body cover 111 that covers the entire optical system of the inspection device 100 shown in FIG. 3 is composed of a thin stainless steel plate and is not constructed with any special vacuum-tight structure. Therefore, the internal space of the body cover 111 is filled with the air. However, the laser light L11 does not attenuate when it propagates through the air. Accordingly, there is no need for the vacuum-tight structure, thus enabling a simpler device configuration. This makes it possible to realize a high-sensitive inspection device at a low price. When the sixth harmonic of a solid-state laser device that oscillates at or near 1064 nm, which is one of the most widely available solid-state laser devices, is used as the inspection light source, the inspection device 100 can be constructed by using a body similar to those of conventional inspection devices without using any vacuum-tight structure.

When a picosecond laser device having a pulse width of about 8 ps is used for the fundamental wave laser light as in the case of this exemplary embodiment, the spectrum width at or near 177 nm, which is the sixth harmonic, becomes about 14 pm. Therefore, the center wavelength of the spectrum profile needs to be away from any absorption lines of oxygen molecules by at least the half width at half maximum, i.e., by at least 7 pm. With consideration given to this, the center wavelength of the sixth harmonic needs to be included in one of the four bands (i.e., in the band [A], [B], [C] or [D]) shown in FIG. 2. The hatched arrows in FIG. 2 indicate that the center wavelengths are 7 pm away from any absorption lines. In this exemplary embodiment, the center wavelength is 177.403 nm and hence included in the band [C]. Needless to say, the center wavelength of the fundamental wave may be included in the band [A] instead of being included in the band [C]. Further, the center wavelength of the fundamental wave may be included in the band [B] or in the band [D].

Figure 5:
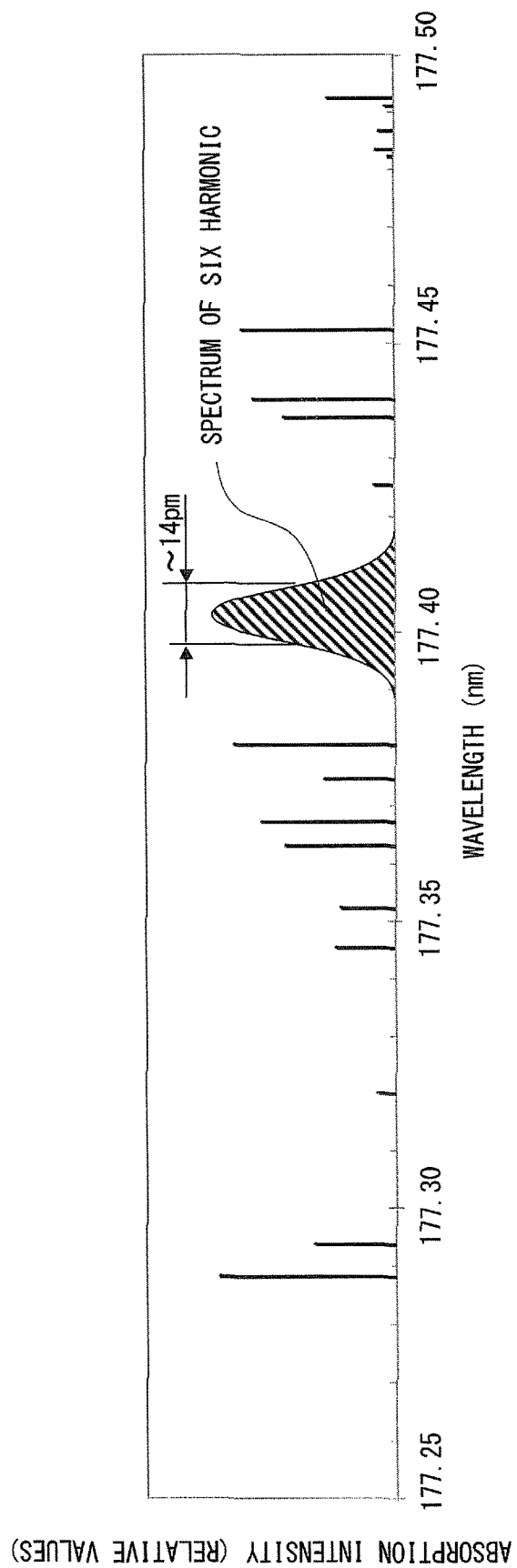
FIG. 5 is a graph showing absorption lines of oxygen molecules and a spectrum of the sixth harmonic, which is used as inspection light.

Note that as shown in FIG. 5, the interval between two absorption lines located on both sides of the center wavelength of 177.034 nm is about 36 pm in this exemplary embodiment. Therefore, if the full width of the spectrum profile is wider than this interval, the laser light is somewhat absorbed by oxygen molecules even when the center wavelength is accurately tuned to the center of the interval. That is, the full width of the spectrum profile is preferably equal to or narrower than about 36 pm. When this is converted for the fundamental wave, it becomes about 532 pm.

Further, with consideration given to Expression (2), the pulse width is preferably adjusted to 3.1 ps or wider as expressed as the full width at half maximum. Therefore, a picosecond laser device is used in this exemplary embodiment. However, even if the full width at half maximum is somewhat narrower than 3.1 ps and an absorption line(s) is included in the skirts of the spectrum profile, the only problem is that the laser power is slightly lowered. That is, it does not cause any substantial problem. That is, any laser device having a pulse width that is equal to or wider than a half of the aforementioned value and equal to or wider than 2 ps can be practically used as a laser device suitable for this exemplary embodiment. That is, any pulsed laser light having a full width at half maximum equal to or larger than 2 ps can be used.

Incidentally, most of the lenses that constitute the objective lens 108 use calcium fluoride ($CaF_2$) having a high transmittance at a wavelength of 177 nm as their glass material. However, since the spectrum width of the ultraviolet light emitted from the laser light source device 200 in this exemplary embodiment is 14 pm and is relatively wide, the objective lens 108 has a function of reducing a chromatic aberration. Therefore, at least one of the lenses constituting the objective lens 108 uses synthetic silica (i.e., quartz) as its glass material. It should be noted that it is not typical synthetic silica but is fluorine-doped synthetic silica. As a result, the objective lens 108 has a high transmittance at the wavelength of 177 nm.

Further, the laser light source device 200 of this exemplary embodiment shown in FIG. 4 generates the second harmonic (SHG) of the third harmonic having a wavelength of 355 nm in order to generate the sixth harmonic having a wavelength of 177 nm. However, the sum frequency of the second harmonic having a wavelength 532 nm and the third harmonic having a wavelength 355 nm, i.e., the fifth harmonic having a wavelength of 213 nm may be first generated, and then the sum frequency of the fifth harmonic and the fundamental wave, i.e., laser light having a wavelength of 177 nm may be generated. That is, two SFG (Sum Frequency Generation) means may be arranged in series behind the BBO crystal 203. Note that a KBBF crystal may be used in place of the RBBF crystal 204. Further, laser light having a wavelength of 177 nm may be generated by performing the sum frequency mixing of the second harmonic having a wavelength of 532 nm and the fourth harmonic having a wavelength of 266 nm by using an RBBF crystal or a KBBF crystal.

Figure 6:
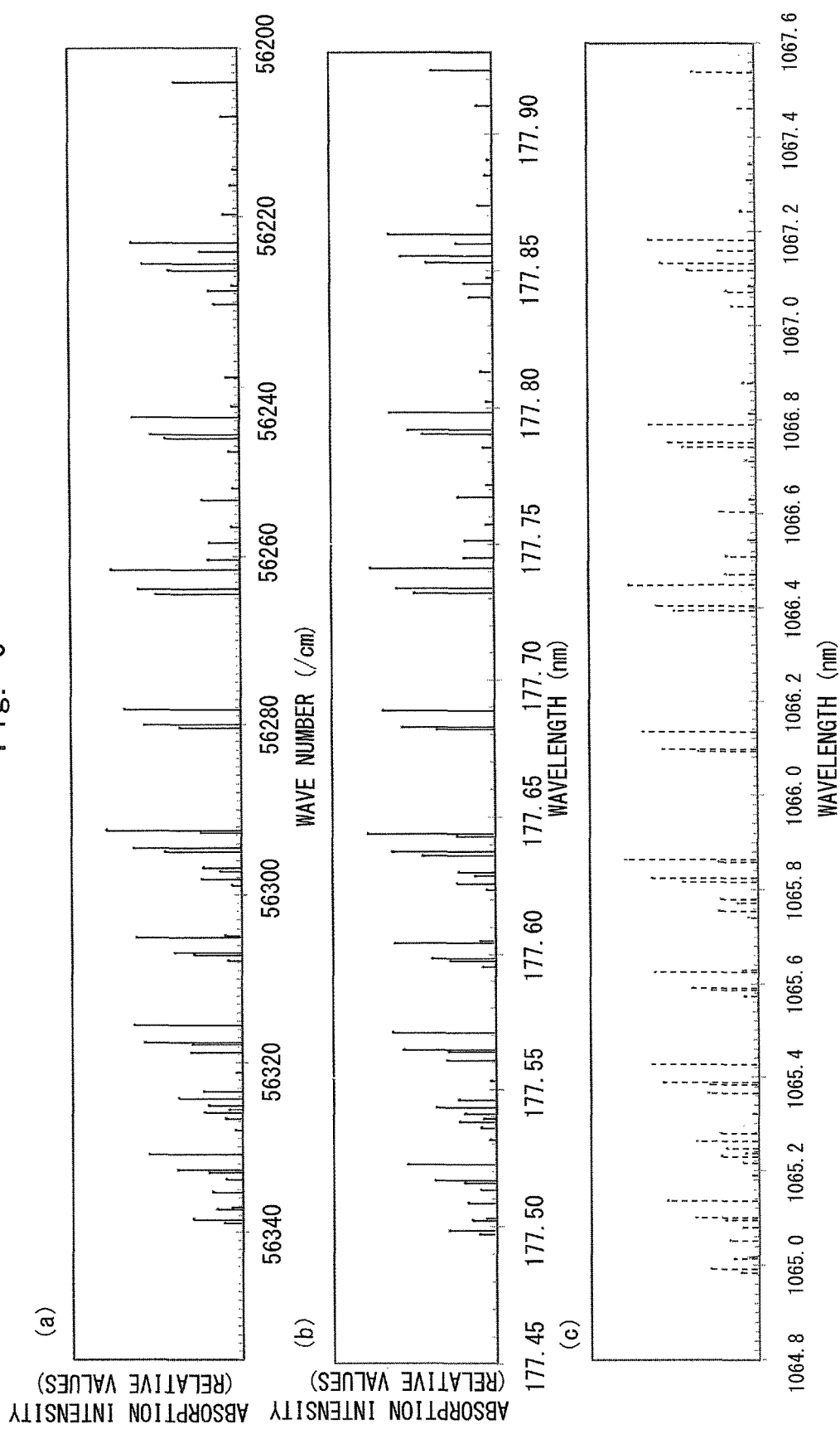
FIG. 6 shows wide-range spectra showing absorption spectra of oxygen molecules and fundamental-wave-converted wavelengths.

In the above-described exemplary embodiments according to the present invention, a solid-state laser device or a fiber laser device that oscillates (i.e., generates) laser light at or near a wavelength of 1064 nm is used as the base component. However, for the fiber laser device, in particular, there are media that can oscillate (i.e., generate) laser light having a wavelength longer than 1064 nm. For example, for wavelengths of 1065 nm to 1067 nm, the wavelengths of their sixth harmonics are from about 177.5 to about 177.9. Therefore, their wave numbers spread from about 56,200 $cm^{-1}$ to about 56,340 $cm^{-1}$. There are a number of absorption lines of oxygen molecules between about 56,200 $cm^{-1}$ to about 56,340 $cm^{-1}$. However, as shown in FIG. 6, there is a range(s) having a width of about 40 pm in which no absorption line is present. Therefore, the fundamental wave may be oscillated so that its center wavelength is included in this range. However, the present invention has a feature that the use of a laser device having a wavelength of 1064 nm, which is one of the most widely available solid-state laser devices, makes the development of an inspection device easier.

Figure 7:
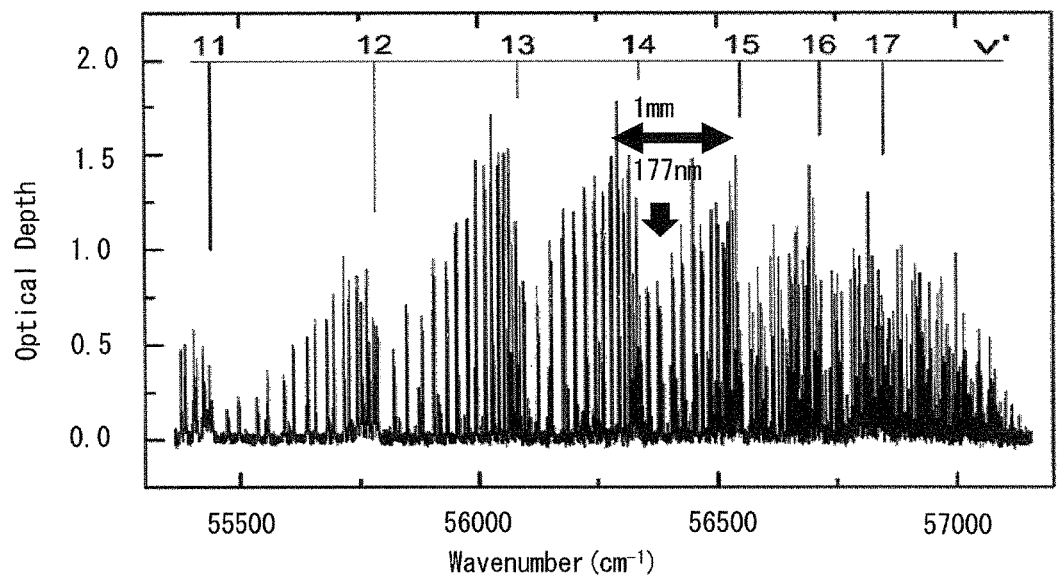
FIG. 7 shows absorption lines of oxygen molecules.
Figure 8:
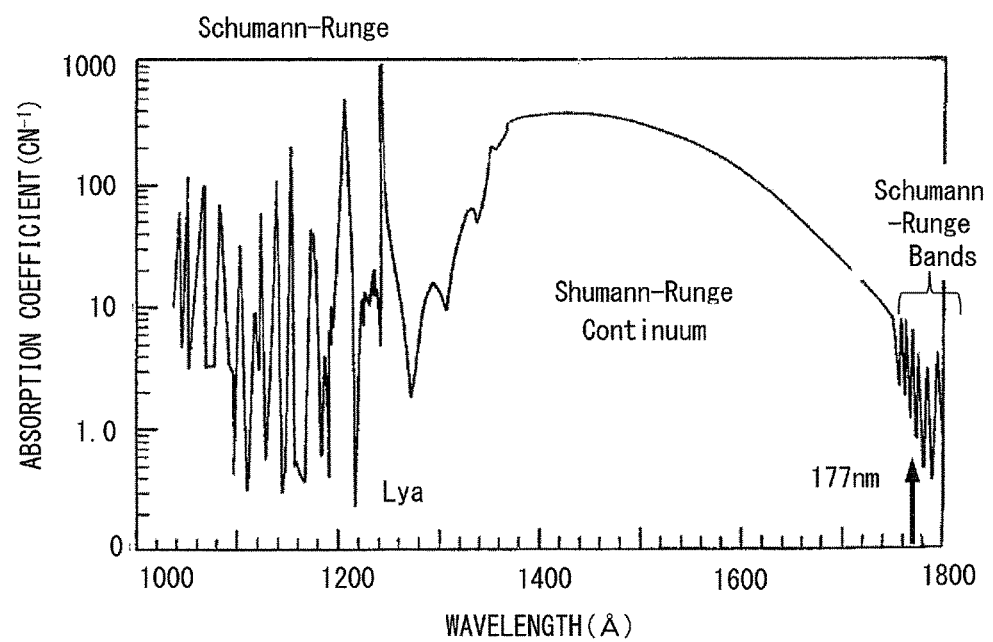
FIG. 8 is a graph showing Shumann-Runge Bands in an absorption spectrum of oxygen molecules.

Further, when the center wavelength is shorter than 177 nm instead of being longer than 177 nm, i.e., when the wave number is equal to or larger than 56,500 cm$^{-1}$, the intervals between absorption lines become narrower as shown in an absorption spectrum shown in FIG. 7. Therefore, there are few or no ranges having a width of several tens pm, which corresponds to the spectrum width of the picosecond laser device, in which no absorption line is present. Therefore, a fundamental wave having a wavelength of 1064 nm, whose sixth harmonic has a wavelength of 177 nm, is preferably used in the present invention.

Although the pulsed laser light emitted from the inspection device 100 has a wavelength in a VUV (Vacuum UltraViolet) range, the pulsed laser light can be used in the atmosphere. That is, it is possible to allow laser light at or near 177 nm efficiently propagate even through a gas atmosphere containing oxygen. A Yb-doped fiber laser device can be used as the solid-state laser device that generates the fundamental wave. Alternatively, a mode-locked laser device using an Nd:YVO4 crystal can be also used as the solid-state laser device that generates the fundamental wave. Further, a mode-locked laser device using an Nd:YAG crystal can be also used as the solid-state laser device that generates the fundamental wave. By using these solid-state laser devices, it is possible to oscillate (i.e., generate) a high-power fundamental wave whose center wave is included in one of the bands [A] to [D]. Further, the repetition frequency can be increased to a 1 MHz or higher.

Further, the inspection device 100 uses the laser light L11 emitted from the laser light source device 200 as illumination light. By doing so, the inspection device 100 can be constructed by using a simple body similar to those used in the related art. The wavelength at or near 177 nm can improve the resolution by about 10% in comparison to a conventional inspection device using a wavelength of 193 nm Therefore, it is possible to perform an inspection with higher sensitivity than that in a related art device at substantially the same cost as that of the related art device. Further, it is possible to use the laser light source device 200 for an inspection device other than the mask inspection device, such as a semiconductor device inspection device and a semiconductor wafer inspection device. In particular, by using a laser light source device 200 having a repetition frequency of 1 MHz or higher in an inspection device in which a TDI camera is used as the optical detector, the fluctuations can be reduced. Further, the laser light source device 200 may be also used for an application other than the inspection device, such as an exposure device.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A laser light source device comprising:
a Quasi Continuous Wave (QCW) solid-state laser device that oscillates laser light including a fundamental wave with its center wavelength being included in a range between 1063.805 nm and 1063.878 nm, the QCW solid-state laser device having a repetition frequency of 1 MHz or higher; and
means for generating a sixth harmonic of pulsed laser light extracted from the solid-state laser device, wherein the sixth harmonic has a wavelength of approximately 177 nm, and
the means includes:
a first optical crystal that generates a second harmonic of the fundamental wave, and is an LiB$_3$O$_5$ crystal,
a second optical crystal that generates a third harmonic of the fundamental wave, and is a β-BaB$_2$O$_4$ crystal, the third harmonic having a sum of a frequency of the fundamental wave and a frequency of the second harmonic, and
a third optical crystal that generates the sixth harmonic of the fundamental wave, and is an RbBe$_2$BO$_3$F$_2$ crystal or KBe$_2$BO$_3$F$_2$ crystal, the sixth harmonic being a second harmonic of the third harmonic.

2. A laser light source device comprising:
a Quasi Continuous Wave (QCW) solid-state laser device that oscillates laser light including a fundamental wave with its center wavelength being included in a range between 1063.962 nm and 1064.031 nm, the QCW solid-state laser device having a repetition frequency of 1 MHz or higher; and
means for generating a sixth harmonic of pulsed laser light extracted from the solid-state laser device, wherein the sixth harmonic has a wavelength of approximately 177 nm, and
the means includes:
a first optical crystal that generates a second harmonic of the fundamental wave, and is an LiB$_3$O$_5$ crystal,
a second optical crystal that generates a third harmonic of the fundamental wave, and is a β-BaB$_2$O$_4$ crystal, the third harmonic having a sum of a frequency of the fundamental wave and a frequency of the second harmonic, and
a third optical crystal that generates the sixth harmonic of the fundamental wave, and is an RbBe$_2$BO$_3$F$_2$ crystal or KBe$_2$BO$_3$F$_2$ crystal, the sixth harmonic being a second harmonic of the third harmonic.

3. A laser light source device comprising:
a Quasi Continuous Wave (QCW) solid-state laser device that oscillates laser light including a fundamental wave with its center wavelength being included in a range between 1064.757 nm and 1064.852 nm, the QCW solid-state laser device having a repetition frequency of 1 MHz or higher; and
means for generating a sixth harmonic of pulsed laser light extracted from the solid-state laser device, wherein the sixth harmonic has a wavelength of approximately 177 nm, and
the means includes:
a first optical crystal that generates a second harmonic of the fundamental wave, and is an LiB$_3$O$_5$ crystal,
a second optical crystal that generates a third harmonic of the fundamental wave, and is a β-BaB$_2$O$_4$ crystal, the third harmonic having a sum of a frequency of the fundamental wave and a frequency of the second harmonic, and
a third optical crystal that generates the sixth harmonic of the fundamental wave, and is an RbBe$_2$BO$_3$F$_2$ crystal or KBe$_2$BO$_3$F$_2$ crystal, the sixth harmonic being a second harmonic of the third harmonic.

4. The laser light source device according to claim 1, wherein a pulse width of the pulsed laser light is equal to or greater than 2 picoseconds.

5. The laser light source device according to claim 1, wherein an Yb-doped fiber laser device, a mode-locked solid-state laser device using an Nd:YVO4 crystal, or a mode-locked solid-state laser device using an Nd:YAG crystal is used as the solid-state laser device.

6. An inspection device comprising:
   a light source device according to claim 1; and
   a photodetector that takes an image of a sample illuminated by the sixth harmonic generated by the laser light source device.

7. The inspection device according to claim 6, wherein the photodetector is a Time Delay Integration camera.

* * * * *